(12) United States Patent
Casoli et al.

(10) Patent No.: US 11,643,639 B2
(45) Date of Patent: May 9, 2023

(54) SKIN RECONSTRUCTION METHOD

(71) Applicants: UNIVERSITÉ DE BORDEAUX, Bordeaux (FR); INSERM, Paris (FR); CENTRE HOSPITALIER UNIVERSITAIRE DE BORDEAUX, Talence (FR)

(72) Inventors: Vincent Casoli, Lège-Cap-Ferret (FR); Muriel Cario-André, Pessac (FR); Jean-Christophe Lepivert, Bordeaux (FR)

(73) Assignees: UNIVERSITÉ DE BORDEAUX, Bordeaux (FR); INSERM, Paris (FR); CENTRE HOSPITALIER UNIVERSITAIRE DE BORDEAUX, Talence (FR)

( * ) Notice: Subject to any disclaimer, the term of this patent is extended or adjusted under 35 U.S.C. 154(b) by 0 days.

(21) Appl. No.: 15/561,961

(22) PCT Filed: Mar. 25, 2016

(86) PCT No.: PCT/EP2016/056700
§ 371 (c)(1),
(2) Date: Sep. 26, 2017

(87) PCT Pub. No.: WO2016/151133
PCT Pub. Date: Sep. 29, 2016

(65) Prior Publication Data
US 2018/0112188 A1    Apr. 26, 2018

(30) Foreign Application Priority Data

Mar. 26, 2015   (EP) .................................... 15305441

(51) Int. Cl.
*C12N 5/071*    (2010.01)
*A61L 27/60*    (2006.01)
(Continued)

(52) U.S. Cl.
CPC ............ *C12N 5/0698* (2013.01); *A61K 35/35* (2013.01); *A61K 35/36* (2013.01); *A61L 27/24* (2013.01);
(Continued)

(58) Field of Classification Search
CPC .............. C12N 5/0698; C12N 2500/32; C12N 2533/54; C12N 2500/38; C12N 2501/905;
(Continued)

(56) References Cited

U.S. PATENT DOCUMENTS 5,755,814 A * 5/1998 Berg ..................... C12N 5/0698
435/347
6,110,208 A * 8/2000 Soranzo .................. A61L 27/20
424/422

(Continued)

FOREIGN PATENT DOCUMENTS

EP    0282746 A1 * 9/1988    ............. A61L 27/36
EP    0282746 A1    9/1988
(Continued)

OTHER PUBLICATIONS

Pearson growth curve (Year: 2006).*
(Continued)

*Primary Examiner* — Blaine Lankford
*Assistant Examiner* — Lauren K Van Buren
(74) *Attorney, Agent, or Firm* — Kenealy Vaidya LLP

(57) ABSTRACT

Some embodiments are directed to a method for preparing a skin substitute, a dermal substitute, to a skin substitute, to a dermal substitute and to a kit for implementing the method. Some other embodiments are directed to a graft that can consist of of a skin substitute and to the use thereof as treating a skin disorder and/or a loss of skin substance.

13 Claims, 6 Drawing Sheets

(51) Int. Cl.
  *A61L 27/24* (2006.01)
  *A61L 27/38* (2006.01)
  *A61P 17/02* (2006.01)
  *A61P 35/00* (2006.01)
  *A61K 35/35* (2015.01)
  *A61K 35/36* (2015.01)

(52) U.S. Cl.
  CPC ....... *A61L 27/3804* (2013.01); *A61L 27/3813* (2013.01); *A61L 27/3886* (2013.01); *A61L 27/60* (2013.01); *A61P 17/02* (2018.01); *A61P 35/00* (2018.01); *C12N 2500/32* (2013.01); *C12N 2500/38* (2013.01); *C12N 2501/905* (2013.01); *C12N 2502/091* (2013.01); *C12N 2502/094* (2013.01); *C12N 2502/1323* (2013.01); *C12N 2533/54* (2013.01)

(58) Field of Classification Search
  CPC ........ C12N 2502/091; C12N 2502/094; C12N 2502/1323; A61P 17/02; A61P 35/00; A61P 35/36; A61K 35/35; A61K 35/36; A61L 27/3804; A61L 27/24; A61L 27/3813; A61L 27/3886; A61L 27/60
  See application file for complete search history.

(56) References Cited

U.S. PATENT DOCUMENTS

| | | | |
|---|---|---|---|
| 2004/0013652 A1* | 1/2004 | Marko | A61K 35/34 424/93.7 |
| 2007/0087320 A1* | 4/2007 | Licari | A01N 1/02 435/1.1 |
| 2009/0061512 A1* | 3/2009 | Gogly | C12N 5/0656 435/366 |
| 2009/0257986 A1* | 10/2009 | Hunziker | A61L 27/60 424/93.7 |
| 2009/0298042 A1 | 12/2009 | Noll et al. | |
| 2013/0274190 A1* | 10/2013 | Wang | A61L 27/3813 514/9.4 |
| 2014/0287020 A1* | 9/2014 | Boyce | A61P 17/02 424/443 |

FOREIGN PATENT DOCUMENTS

| | | | |
|---|---|---|---|
| EP | 2103687 B1 | 7/2016 | |
| JP | H10-509735 A | 9/1998 | |
| JP | 2009-219491 A | 10/2009 | |
| WO | WO96/19099 A2 | 6/1996 | |
| WO | WO-2007061168 A1 * | 1/2007 | |
| WO | WO-2007061168 A1 * | 5/2007 | ............ A61P 17/00 |

OTHER PUBLICATIONS

Bottcher-Haberzeth "Tissue Engineering of the skin" Burns 36 (2010) 450-460. (Year: 2010).*

Tammi et al. "Hyaluronan in the Epidermis" Jun. 15, 1998 (Year: 1998).*

Hayato, N., et al., "Development of novel wound dressing composed of hyaluronic acid and collagen sponge containing epidermal growth factor and vitamin C derivative," J. Artificial Organs 2013;17(1):81-87.

International Search Report for PCT Patent App. No. PCT/EP2016/056700 dated May 4, 2016 with English language translation thereof.

Written Opinion for PCT Patent App. No. PCT/EP2016/056700 dated May 4, 2016.

Nakazawa et al., "Pigmented Human Skin Equivalent: New Method of Reconstitution by Grafting an Epithelial Sheet Onto a Non-Contractile Dermal Equivalent," Pigment Cell Research 1997, v10(6), p. 382-390, United States.

* cited by examiner

A

B

C

A

B

SKIN RECONSTRUCTION METHOD

CROSS REFERENCE TO RELATED APPLICATION(S)

This application is a national phase filing under 35 C.F.R. § 371 of and claims priority to PCT Patent Application No. PCT/EP2016/056700, filed on Mar. 25, 2016, which claims the priority benefit under 35 U.S.C. § 119 of European Patent Application No. 15305441.6, filed on Mar. 26, 2015, the contents of each of which are hereby incorporated in their entireties by reference.

BACKGROUND

The presently disclosed subject matter relates to a method for preparing a skin substitute, to an animal skin substitute, or a mammalian and/or human skin substitute, which can be obtained by implementing the method and to a kit for implementing the method.

The presently disclosed subject matter also relates to a graft that can consist of a skin substitute and to the use thereof for treating a skin disorder and/or a loss of skin substance.

The presently disclosed subject matter can be used in particular in the pharmacological, medical and clinical fields.

In the description below, the references between square brackets ([ ]) refer back to the list of references presented at the end of the text.

The skin is a very complex organ including a very particular stratified structure. It includes three main parts:
 a superficial part, which is the thinnest, called the epidermis,
 a thicker internal part, the dermis, to which the epidermis is attached, and
 a deeper layer, the hypodermis.

It in particular provides a barrier between the external media and the internal medium of many mammals, including in particular human beings. By virtue of this "barrier" function, the skin naturally provides protection for the organism while at the same time providing communication between said organism and the external environment. The skin constitutes the first organ of defense against any attack.

The skin is subjected to many attacks; they can for example be attacks associated with UV rays that can lead to inflammatory reactions/cell modifications responsible for cancers, physical attacks such as burns, scarifications, for example due to blunt objects, chemical attacks, for example associated with chemical products, for example detergents. These various attacks can in particular induce skin disorders capable of modifying the structure of the skin, of altering its coloration and/or of causing the appearance of skin wounds.

It is in fact known that chemical products and/or molecules such as hydroquinone, when they are used at high doses, can induce strong depigmentation, can cause scars, stretch marks, serious pathological conditions, for example diabetes, hypertension, skin cancers or systemic complications, kidney disorders, the development of pilosity and can cause beard growth and a disturbance of body odor. When the decoloration goes beyond the desired effect, these consequences can be irreversible. The principal solution then remains a skin graft in order to try to "return to" a normal appearance.

Other elements can be responsible for an alteration of the skin, for example parameters of genetic order and/or parameters associated with systemic endocrine and/or autoimmune disorders. They can in particular be pathological conditions which cause a pigment disorder, such as vitiligo, hypermelanosis, hypomelanosis or a nevus. One of the methods for treating such disorders includes a skin graft and/or the implementation of pigmentary cells. However, these methods have relative efficacies often associated with the stability of the skin and/or pigmentary cells applied.

The skin can also be injured, for example by external elements such as blunt objects, causing more or less deep wounds. The skin has very considerable regeneration and healing capacities which most of the time allow healing in the more or less long term. The healing time and/or capacity can depend in particular on the depth/extent of the wound and also on the physiological condition of the individual. Indeed, in the case of deep wounds, they can represent "open doors" to pathogens, requiring increased monitoring and/or the need to intervene in order to close the wound, for example with sutures or by applying a skin graft thereto in order to in particular enable the skin to regenerate, in particular to repair the various damaged parts.

In the related art, there are artificial dermal substitutes which in particular temporarily allow the formation of an environment favorable for skin regeneration. The structure and the environment formed by these substitutes are often close to those of the dermis. However, these substitutes are medical devices, which are essentially synthetic and expensive.

There are also in the related art systems for culturing cells, in particular keratinocytes, obtained from a skin sample from an individual, which after several weeks form a culture which can be deposited/sprayed onto a wound, for example a chronic wound or a burn, in order to promote the healing thereof.

However, these methods and substitutes do not as such constitute skin substitutes including the constitutive predominant cells of the skin, such as fibroblasts, keratinocytes and melanocytes. In particular, these substitutes do not include melanocytes and do not therefore make it possible to obtain skin substitutes which are pigmented and/or capable of being pigmented. Furthermore, these substitutes cannot be used for example for the treatment of pigmentary disorders, the treatment of deep wounds, for example due to surgical procedures, accidents causing for example a significant loss of skin that can go as far as the total skin loss.

Moreover, the methods for obtaining the available dermal substitutes are "slow" methods which do not for example make it possible to obtain substitutes in periods of time compatible with the treatment of specific wounds such as deep burns.

Finally, the majority of the commercially available skin substitutes are products that are fragile both in structural terms and in epidemiological terms. Thus, these products are often small in size in order in particular to avoid any tearing of the product during handling thereof.

There are also in the related art systems/methods for preparing skin substitutes, for example as described in document U.S. Pat. No. 5,755,814, including in particular the culture of cells, in particular fibroblasts, and/or of a mixture of melanocytes and keratinocytes. However, these systems/methods do not make it possible to obtain a substitute with a structure identical to that of the skin in vivo. In addition, the substitutes obtained by these methods exhibit parakeratosis, which is a skin differentiation abnormality, corresponding to abnormal maturation of the keratin in the horny layer which does not therefore allow them to be used in the treatment of skin disorders and/or losses of skin substance. Finally, the known systems/methods for preparing skin substitutes use in particular media including compounds which are incompatible with clinical use, for example bovine pituitary extract.

There is therefore a real need to find a method for preparing a skin substitute which overcomes these faults, drawbacks and obstacles of the related art, in particular a method which makes it possible to obtain a skin substitute including the major constituent cells of the skin, in particular the fibroblasts, keratinocytes and melanocytes, for reducing the costs and the preparation time of the substitute.

There is also a real need in the related art to find a method which allows the production of a reproducible and reliable skin model.

There is also a real need to find a novel skin substitute that can be used for the treatment of skin disorders and/or of losses of skin substance.

There is also a real need to find a novel skin substitute which can be easily handled and which does not exhibit a high risk of tearing during handling thereof.

SUMMARY

An aspect of the presently disclosed subject matter is specifically to meet this need by providing a method for preparing a skin substitute, including the following steps:
  a. culture of fibroblasts in a fibroblast culture medium M1;
  b. seeding of a matrix including collagen with fibroblasts resulting from step a;
  c. culture of the fibroblasts seeded in the matrix including collagen in a fibroblasts culture medium M2 including ascorbic acid or an ascorbate or a derivative thereof, the matrix and the fibroblasts cultured forming a dermal substitute;
  d. culture of melanocytes in a melanocyte culture medium M3;
  e. culture of keratinocytes in a keratinocyte culture medium M4;
  f. mixing of melanocytes obtained in step d with keratinocytes obtained in step e;
  g. seeding of the dermal substrate obtained in step c with the mixture obtained in step f;
  h. culture of the dermal substitute seeded in step g in a skin culture medium M5 thus forming the skin substitute.

In the presently disclosed subject matter, the term "include" can mean equally, on the one hand, "include", "contain" or "encompass" and, on the other hand, "constituted of" or "consist of".

In the presently disclosed subject matter, the dermal substitute obtained according to the method of some embodiments is a complete tissue which reproduces the characteristics of a dermis in vivo, namely which includes macromolecules of protein type, in particular collagen fibers, glycosaminoglycan fibers, proteins and functional fibroblasts.

In the presently disclosed subject matter, the skin substitute obtained according to the method of some embodiments is a complete tissue which reproduces the characteristics of a skin in vivo, namely which includes a keratinized pluristratified epithelium including keratinocytes reproducing a stratum basal, a stratum spinosum, a stratum granulosum and a stratum corneum which are histologically normal, and basal melanocytes in contact with a dermal substitute containing functional fibroblasts, via a functional basal lamina.

Advantageously, the method according to some embodiments make it possible to obtain a skin substitute including a basal lamina that can consist in particular of a protein mixture secreted by the cells of the substitute thus forming a dermal-epidermal junction reproducing the characteristics of a skin in vivo.

In the presently disclosed subject matter, the fibroblasts, melanocytes and keratinocytes that can be used in the method of some embodiments can be all or most fibroblasts, melanocytes and keratinocytes known to those with ordinary skill in the art. They can for example be fibroblasts, melanocytes and/or keratinocytes obtained from cell banks, for example originating from the Collection Nationale de Culture de Microorganisme [French National Collection of Microorganism Cultures] (CNCM) of the Institut Pasteur, 25 rue du Docteur Roux, F-75724 Paris Cedex 15. They can also be commercially available fibroblasts, melanocytes and/or keratinocytes, for example the cells sold by the company Thermofischer scientific, the company CellnTec or the company Promocell. They can also be fibroblasts, melanocytes and/or keratinocytes isolated from a biological sample from an animal, or a mammal and/or from a human being, isolated beforehand. The fibroblasts, melanocytes and/or keratinocytes can be fibroblasts, melanocytes and/or keratinocytes isolated independently from a biopsy or several biopsies. The fibroblasts, melanocytes and/or keratinocytes can be isolated independently from a biopsy or several biopsies from an individual, or a mammal and/or a human being, for the purpose of a graft of said skin substitute onto said patient. They can independently be fibroblasts, melanocytes and/or keratinocytes which are autologous or heterologous with respect to an individual.

In the presently disclosed subject matter, advantageously at least two cell types among the three cell types represented by the fibroblasts, melanocytes and keratinocytes are autologous with respect to an individual.

In one particular embodiment, the fibroblasts, melanocytes and keratinocytes are advantageously cells which are autologous with respect to an individual.

The fibroblasts, melanocytes and/or keratinocytes can be isolated independently from a biopsy or several biopsies originating, for example, from Caucasian, Asian or African skin, from various anatomical sites, for example from the back, face, breast, back of the hands, palms of a human being.

They can independently be fibroblasts, melanocytes and/or keratinocytes independently isolated from skin biopsies, for example, from a human being, having one or more pathological skin conditions, for example age spots (actinic lentigo), melasma, vitiligo, nevus or melanoma.

They can also be fibroblasts, melanocytes and/or keratinocytes which have been independently genetically modified, for example with retroviruses, lentiviruses, adenoviruses, adeno-associated viruses (AAVs). They can for example be fibroblasts, melanocytes and/or keratinocytes independently overexpressing at least one protein, for example a protein chosen from collagen VII, keratins 5, 14, catalase and SIRT6, and/or underexpressing at least one protein, for example via the small hairpin RNA (shRNA) or small interfering RNA (siRNA) technique, for example collagen VII, HIF1 or CCN3. They can for example be fibroblasts, melanocytes and/or keratinocytes which have been independently genetically modified as described in Pendaries V et al., JID 2012 [1]; Petek L M et al. Mol ther 2010 [2]. They can for example be fibroblasts, melanocytes and/or keratinocytes which can or cannot have been independently genetically modified, for example the Ker-CT cell identified under the reference ATCC CRL-4048, or the TelCOFS02MA cell identified under the reference ATCC CRL-4005.

They can also be fibroblasts, melanocytes and/or keratinocytes derived from a cell line, for example the HaCaT keratinocyte line, or the WS1 fibroblast line.

The fibroblasts that can be used do not necessarily include irradiated 3T3 fibroblasts.

They can also be fibroblasts, melanocytes and/or keratinocytes independently obtained from adult stem cells, from pluripotent stem cells induced, for example, by maintaining said adult stem cells, and/or from pluripotent stem cells induced via, for example, the introduction of Oct3/4, Sox 2, KLF4 or c-Myc genes and then differentiated by means of factor cocktails, for example retinoic acid and/or BMP-4, into a cell line. They can also be adult stem cells and/or pluripotent stem cells induced by non-viral techniques based on the use of nanoparticles, for example arginine-terminated polyamidoamine nanoparticles. Those with ordinary skill in the art, by virtue of their general knowledge, will be able to choose the method and/or the cells. They can for example be fibroblasts, melanocytes and/or keratinocytes obtained by the method described in Kogut et al. Methods Mol Biol 2014 [3], in Ohta et al., Methods Mol Biol, 2013 [4], and/or in Revilla et al., J Tissue Eng Regen Med, 2015 [5].

In the presently disclosed subject matter, the term "fibroblast culture medium M1" is intended to mean any medium known to those with ordinary skill in the art that are suitable for the culture of fibroblasts. It can for example be a commercially available medium, for example a Dulbecco's modified Eagle's minimal essential medium (DMEM) sold by the company Gibco, including in particular a mixture of amino acids, of vitamins, of inorganic salts and of sugars (for example glucose, or a Fibrolife medium sold by the company Cell Systems.

TABLE 1 composition of Dulbecco's modified Eagle's minimal essential medium (DMEM)

| Composition | Concentration (mg/l) |
|---|---|
| Amino acids | |
| Glycine | 84 |
| L-Arginine hydrochloride | 84 |
| L-Cystine 2HCl | 63 |
| L-Glutamine | 580 |
| L-Histidine hydrochloride-$H_2O$ | 42 |
| L-Isoleucine | 105 |
| L-Leucine | 105 |
| L-Lysine hydrochloride | 146 |
| L-Methionine | 30 |
| L-Phenylalanine | 66 |
| L-Serine | 42 |
| L-Threonine | 95 |
| L-Tryptophan | 16 |
| L-Tyrosine | 72 |
| L-Valine | 94 |
| Vitamins | |
| Choline chloride | 4 |
| D-Calcium pantothenate | 4 |
| Folic acid | 4 |
| Niacinamide | 4 |
| Pyridoxine hydrochloride | 4 |
| Riboflavin | 0.4 |
| Thiamine hydrochloride | 4 |
| i-Inositol | 7.2 |
| Inorganic salts | |
| Calcium chloride ($CaCl_2$—$2H_2O$) | 264 |
| Ferric Nitrate ($Fe(NO_3)_3 9H_2O$) | 0.1 |

TABLE 1-continued composition of Dulbecco's modified Eagle's minimal essential medium (DMEM)

| Composition | Concentration (mg/l) |
|---|---|
| Magnesium sulfate ($MgSO_4$—$7H_2O$) | 200 |
| Potassium chloride (KCl) | 400 |
| Sodium bicarbonate ($NaHCO_3$) | 3700 |
| Sodium chloride (NaCl) | 6400 |
| Monobasic sodium phosphate ($NaH_2PO_4$—$2H_2O$) | 141 |
| Other compounds | |
| D-Glucose (Dextrose) | 1000 |
| Sodium Pyruvate | 110 |

In the presently disclosed subject matter, the medium M1 can also include supplements, in particular fetal calf serum (FCS).

In the presently disclosed subject matter, the medium M1 can for example include from 5% to 15% by weight, from 7.5 to 12.5% by weight, 10% by weight of fetal calf serum (FCS) relative to the total weight of the medium.

In the presently disclosed subject matter, the medium M1 can include at least one antifungal and/or antibiotic compound. This can for example be any antifungal and/or antibiotic compound known to those with ordinary skill in the art and/or commercially available. It can for example be at least one antifungal compound chosen from the group including amphotericin B, ketoconazole and a mixture thereof. It can for example be at least one antibiotic compound chosen from the group including penicillin, streptomycin, ciprofloxacin and a mixture thereof.

In the presently disclosed subject matter, the medium M1 can include from 0.1% to 10% by weight, from 0.5% to 5% by weight, 1% by weight of antifungal agent relative to the total weight of the medium.

In the presently disclosed subject matter, the medium M1 can include from 0.1% to 10% by weight, from 0.5% to 5% by weight, 1% by weight of antibiotics relative to the total weight of the medium.

In the presently disclosed subject matter, the medium M1 and/or all or most of the constituents thereof can be of clinical grade.

The term "of clinical grade" denotes in the presently disclosed subject matter the fact that the component or the medium has been recognized by the relevant authority as being suitable for use clinically on a given territory. Advantageously in the presently disclosed subject matter, when the medium is of clinical grade, it does not include bovine pituitary extract.

In the presently disclosed subject matter, the fibroblast culture step a. can be carried out at a temperature included from 30 to 40° C., from 35 to 39° C., or equal to 37° C.

In the presently disclosed subject matter, the fibroblast culture time of step a. can include from 5 to 21 days, from 5 to 15 days, or from 8 to 15 days.

In the presently disclosed subject matter, the fibroblast culture time of step a. can be carried out under a controlled atmosphere including from 5% to 10% of $CO_2$, for example under an atmosphere including at least 5% of $CO_2$.

According to some embodiments, the fibroblast culture step a. can be carried out in an incubator at a temperature from 30 to 40° C., from 32 to 40° C., or equal to 37° C. and under a controlled atmosphere including at least 5% of $CO_2$.

According to some embodiments, the fibroblast culture step a. can be carried out in any suitable culture container known to those with ordinary skill in the art. It can be a petri dish, or a culture flask with a capacity of from 25 to 75 cm$^2$, of 25, 75 or 175 cm$^2$.

According to some embodiments, the fibroblasts obtained by culture according to step a. can form a layer of cells at confluence in the culture container. For example, the fibroblasts can be at 70% to 100% confluence, for example, at 100% confluence.

According to some embodiments, when the culture according to step a. corresponds to a layer of cells optionally at confluence, the method can also include:
- a step a' of removal of the culture medium, rinsing of the cells with a solution, and removal of the rinsing solution,
- a step a" of detachment of the cells by trypsinization, and
- a step a''' of pelleting or centrifugation.

According to some embodiments, in step a', the removal of the culture medium can be carried out by any suitable method known to those with ordinary skill in the art. It can for example be suctioning of the medium, or turning the container upside-down in order to remove the culture medium.

According to some embodiments, in step a', the rinsing of the cells can be carried out by any method known to those with ordinary skill in the art, for example by dipping, sprinkling, or incubation of the cells in a rinsing solution.

In the presently disclosed subject matter, the term "rinsing solution" is intended to mean any solution for rinsing cells that is known to those with ordinary skill in the art. It can for example be an HBSS (Hank's Balanced Salt Solution) buffer solution at a pH included from 7.2 to 7.4.

TABLE 2 composition of the HBSS medium

| Compounds | Molecular weight g/mol | Concentration (mg/l) | mM |
|---|---|---|---|
| Inorganic salts | | | |
| Potassium chloride | 75 | 400 | 5.333335 |
| Monobasic potassium phosphate (KH$_2$PO$_4$) | 136 | 60 | 0.4411 |
| Sodium bicarbonate | 84 | 350 | 4.16 |
| Sodium chloride | 58 | 8000 | 137.93 |
| Anhydrous dibasic sodium phosphate (Na$_2$HPO$_4$) | 142 | 48 | 0.338 |
| Other compounds | | | |
| D glucose (Dextrose) | 180 | 1000 | 5.55 |
| Phenol red | 376.4 | 10 | 0.0265 |

It can also be a commercially available buffer solution, for example a phosphate buffered saline (PBS), or a Hank's balanced solution sold respectively by the company Gibco, Sigma Aldrich or Lonza.

According to some embodiments, in step a', the removal of the rinsing solution can be carried out by any suitable method known to those with ordinary skill in the art. It can for example be suctioning of the rinsing solution, or turning the container upside-down in order to remove the rinsing solution.

According to some embodiments, the trypsinization step a" can be carried out by immersion of the cells in a buffer solution (BS) including trypsin, followed by the addition of fetal calf serum (FCS) in order to stop the enzymatic reaction.

According to some embodiments, the buffer solution (BS) can be any buffer solution known to those with ordinary skill in the art that can be used in a trypsinization method. It can for example be a phosphate buffered saline (PBS), or a Hank's balanced solution sold respectively by the company Gibco, Sigma Aldrich or Lonza.

According to some embodiments, the amount of trypsin added to the buffer solution (BS) can be between 0.01% and 0.05% by weight relative to the total weight.

According to some embodiments, the incubation time in the buffer solution including trypsin before addition of FCS to the buffer solution (BS) can be between 2 and 10 min.

According to some embodiments, the amount of FCS added to the buffer solution (BS) can be included from 5% to 20% by volume relative to the total volume.

According to some embodiments, the pelleting step a''' can be carried out by any method known to those with ordinary skill in the art. It can for example be a sedimentation or a centrifugation at a speed of 800 to 1400 revolutions per minute, for example equal to 1200 revolutions per minute.

According to some embodiments, the centrifugation step a''' can be carried out for a period of 4 to 10 min, for example equal to 5 minutes.

According to some embodiments, the pelleting step a''' can be carried out by any device known to those with ordinary skill in the art. It can for example be a rotary centrifuge sold by the company Eppendorf or Jouan.

In the presently disclosed subject matter, the term "matrix including collagen" is intended to mean any matrix including collagen that is known to those with ordinary skill in the art and that can be seeded with cells. It can for example be a matrix of collagen corresponding to a non-taut type I collagen gel, not imposing any preferential organization of the fibroblasts, as described in Bell et al., 1979 [6]. It can for example be a matrix with a density/concentration of collagen, for example, of type I collagen, with a surface area of from 25 to 500 cm$^2$. It can for example be a matrix including commercially available collagen, for example it can be a matrix including collagen sold by the company Integra.

Advantageously, the matrix including collagen can be a dermal regeneration matrix. The dermal regeneration matrix can in particular be chosen from the matrices sold under the names Integra (registered trademark) and Matriderm (registered trademark) by the companies Integra Life Science Corporation and MedSkin Solutions Dr. Suwelack AG respectively. Advantageously, and contrary to the other matrices including collagen, the dermal regeneration matrices such as those mentioned above are already modeled, thereby promoting reconstruction of the skin equivalent.

In one embodiment, the matrix including collagen can be a matrix including crosslinked collagen and at least one glycosaminoglycan, for example chondroitin 6-sulfate. It can for example be the Integra matrix (registered trademark) sold by the company Integralife Sciences and/or the matrix obtained according to the method described in the document Boyce S T et al., 1988 [7].

In another embodiment, the matrix including collagen can be a matrix including fibers of native-structure collagen and of elastin. The term "fibers of native-structure collagen" is intended to mean in particular fibers that have not been chemically crosslinked. The matrix can for example be the Matriderm matrix sold by the company MedSkin Solutions Dr. Suwelack AG and/or the matrix obtained according to the method described in the document Hafemann et al., Burns 1999 [8].

In the presently disclosed subject matter, the thickness of the matrix including collagen can be from 1.0 to 3.0 mm (limits included) before seeding with the fibroblasts. In one particular embodiment, the thickness of the matrix including collagen can be strictly greater than 1.0 mm before seeding with the fibroblasts.

In the presently disclosed subject matter, the seeding of step b. can be carried out by any method known to those with ordinary skill in the art. It can for example be an application, for example by sprinkling a culture medium including the fibroblasts onto the matrix, by deposition by subculturing the cells on the matrix, by pouring of a culture medium including the cells in suspension, or by 3D printing for example as described in Wonhye Lee et al. "Multi-layered culture of human skin fibroblasts and keratinocytes through three-dimensional freeform fabrication." Biomaterials, 2009, March; 30(8):1587-95 [7].

In the presently disclosed subject matter, when step a. includes step a", the method of some embodiments can include, before the seeding step b., a step b1 of resuspension of the centrifuged cells in the medium M1.

In the presently disclosed subject matter, the seeding of step b. of a matrix including collagen can be carried out at a density of from 20 000 to 50 000 fibroblasts/cm$^2$, preferably of 30 000 fibroblasts/cm$^2$ of surface area of the matrix including collagen. In one particular embodiment, the fibroblast density can be strictly less than 50 000 fibroblasts/cm$^2$ of matrix including collagen.

In the presently disclosed subject matter, the fibroblast culture medium M2 can be any medium known to those with ordinary skill in the art suitable for the culture of fibroblasts. It can for example be a commercially available medium, for example a Dulbecco's Modified Eagle's minimal essential medium (DMEM) including in particular a mixture of amino acids, of vitamins, of inorganic salts of sugars, for example, glucose.

In the presently disclosed subject matter, the medium M1 can also include supplements, in particular fetal calf serum (FCS).

In the presently disclosed subject matter, the medium M2 can include from 5 to 15% by weight, from 7.5% to 12.5% by weight, or 10% by weight of fetal calf serum (FCS) relative to the total weight of the medium.

In the presently disclosed subject matter, the medium M2 can include at least one antifungal and/or antibiotic compound. It can for example be any antifungal and/or antibiotic compound known to those with ordinary skill in the art and/or commercially available. It can for example be at least one antifungal compound chosen from the group including amphotericin B, ketoconazole or a mixture thereof. It can for example be at least one antibiotic compound chosen from the group including penicillin, streptomycin, ciprofloxacin and a mixture thereof.

In the presently disclosed subject matter, the medium M2 can include from 0.1% to 10% by weight, from 0.5% to 5% by weight, or 1% by weight of antifungal agent relative to the total weight of the medium.

In the presently disclosed subject matter, the medium M2 can include from 0.1% to 10% by weight, from 0.5% to 5% by weight, or an amount equal to 1% by weight of antibiotics relative to the total weight of the medium.

In the presently disclosed subject matter, the medium M2 can also include ascorbic acid or ascorbate or a derivative thereof. For example, the medium M2 can include ascorbic acid or ascorbate at a concentration of from 20 to 60 mg·mL$^{-1}$, for example from 30 to 55 mg·mL$^{-1}$, or equal to 50 mg·mL$^{-1}$.

In the presently disclosed subject matter, the term "derivative" denotes any derivative of carboxylic acid or carboxylate known to those with ordinary skill in the art. For example, this term can include derivatives such as esters or anhydrides of the corresponding acids.

Advantageously, the ascorbic acid makes it possible in particular to promote remodeling of the matrix including collagen by stimulating collagen synthesis by the fibroblasts.

In the presently disclosed subject matter, the medium M2 and/or all or most of the constituents thereof can be of clinical grade.

In the presently disclosed subject matter, the fibroblast culture step c. can be carried out at a temperature included from 30 to 40° C., from 35 to 39° C., or equal to 37° C.

In the presently disclosed subject matter, the fibroblast culture time of step c. can be from 5 to 12 days, or from 7 to 10 days.

In the presently disclosed subject matter, the fibroblast culture step c. can be carried out under a controlled atmosphere including at least 5% of $CO_2$.

In the presently disclosed subject matter, step c. of culture of the fibroblasts seeded in the matrix including collagen can include:
- a first culture step c' for 18 to 28 days in the presence of a fibroblast culture medium M2$^1$ including neither ascorbic acid nor ascorbate, and
- a second culture step c" for at least two days in the presence of a fibroblast culture medium M2$^2$ including ascorbic acid or an ascorbate or a derivative thereof.

In this embodiment, the fibroblast culture medium M2$^1$ corresponds to the medium M2 as defined above including neither ascorbic acid nor ascorbate nor derivative thereof. In the presently disclosed subject matter, the medium M2$^1$ and/or all or most of the constituents thereof can be of clinical grade.

In this embodiment, the fibroblast culture medium M2$^2$ corresponds to the medium M2 as defined above including ascorbic acid or an ascorbate or a derivative thereof. In the presently disclosed subject matter, the medium M2$^2$ and/or all or most of the constituents thereof can be of clinical grade.

In the presently disclosed subject matter, the culture step c' can be carried out at a temperature included from 30 to 45° C., from 35 to 39° C., or equal to 37° C.

In the presently disclosed subject matter, the culture time of step c'. can be from 19 to 27 hours, for example 24 hours.

In the presently disclosed subject matter, the culture step c". can be carried out at a temperature included from 30 to 40° C., from 35 to 39° C., or equal to 37° C.

In the presently disclosed subject matter, the culture time of step c". can be between 5 and 12 days, or equal to 7 days.

The present disclosure advantageously demonstrates that the matrix and the cultured fibroblasts obtained in step c. form a structure corresponding to a dermal substitute.

Advantageously, the present disclosure also demonstrates that the culture step c' corresponds to a step of adhesion and of colonization of the matrix by the fibroblasts and step c" advantageously allows remodeling of the matrix including the fibroblasts in order to form a dermal substitute. In particular, the succession of steps c' and c" with the use respectively of the media M2$^1$ and M2$^2$ will advantageously make it possible to form a dermal substitute in which the fibroblasts will not proliferate, but colonize the matrix including collagen while at the same time advantageously allowing collagen production by the fibroblasts themselves, thus allowing remodeling of the dermis.

In other words, the product obtained at the end of step c. can be advantageously used as a dermal substitute. In particular, this product can include all or most the physico-chemical characteristics of the dermis from which the fibroblasts can be derived.

According to some embodiments, the melanocyte culture step d. can be carried out in any suitable culture container known to those with ordinary skill in the art. It can be a petri dish, or a culture flask with a capacity of 25 to 75 cm$^2$, of 25, 75 or 175 cm$^2$.

In the presently disclosed subject matter, the melanocyte culture medium M3 can be any medium known to those with ordinary skill in the art that is suitable for the culture of melanocytes. It can for example be a commercially available medium, for example a commercially available medium sold by the company Promocell under the reference "Melanocyte Medium M2", "MBM" sold by the company Promocell, in an MCDB 153 medium sold by the company Sigma-Aldrich including in particular a mixture of amino acids, of vitamins, of inorganic salts of sugars, for example glucose, as represented in table 3 below:

TABLE 3 composition of the MCDB 153 medium

| Composition | Concentration in g · L$^{-1}$ |
|---|---|
| Ammonium Metavanadate | 0.000000585 |
| Anhydrous calcium chloride | 0.00333 |
| Copper Sulfate•5 H$_2$O | 0.00000275 |
| Ferrous sulfate•7 H$_2$O | 0.00139 |
| Magnesium chloride | 0.05713 |
| Manganese Sulfate | 0.000000151 |
| Molybdic Acid•4 H$_2$O (ammonium) | 0.00000124 |
| Nickel Chloride•6 H$_2$O | 0.00000012 |
| Potassium Chloride | 0.11183 |
| Sodium Acetate (anhydrous) | 0.30153 |
| Sodium chloride | 7.599 |
| Sodium Metasilicate•9 H$_2$O | 0.000142 |
| Dibasic Sodium Phosphate (anhydrous) | 0.284088 |
| Sodium Selenite | 0.0000038 |
| Stannous Chloride•2 H$_2$O | 0.000000113 |
| Zinc Sulfate•7 H$_2$O | 0.000144 |
| L-Alanine | 0.00891 |
| L-Arginine•HCl | 0.2107 |
| L-Asparagine•H$_2$O | 0.015 |
| L-Aspartic Acid | 0.00399 |
| L-Cysteine•HCl•H$_2$O | 0.04204 |
| L-Glutamic Acid | 0.01471 |
| L-Glutamine | 0.8772 |
| Glycine | 0.00751 |
| L-Histidine•HCl•H$_2$O | 0.01677 |
| L-Isoleucine | 0.001968 |
| L-Leucine | 0.0656 |
| L-Lysine•HCl | 0.01827 |
| L-Methionine | 0.00448 |
| L-Phenylalanine | 0.00496 |
| L-Proline | 0.03453 |
| L-Serine | 0.06306 |
| L-Threonine | 0.01191 |
| L-Tryptophan | 0.00306 |
| L-Tyrosine•2Na | 0.00341 |
| L-Valine | 0.03513 |
| D-Biotin | 0.0000146 |
| Choline chloride | 0.01396 |
| Folic acid | 0.00079 |
| myo-Inositol | 0.01802 |
| Niacinamide | 0.00003663 |
| D-Pantothenic Acid (hemicalcium) | 0.000238 |
| Pyridoxine•HCl | 0.00006171 |
| Riboflavin | 0.0000376 |
| Thiamine•HCl | 0.000337 |
| Vitamin B-12 | 0.000407 |
| Adenine•HCl | 0.03088 |

TABLE 3-continued composition of the MCDB 153 medium

| Composition | Concentration in g · L$^{-1}$ |
|---|---|
| D-Glucose | 1.081 |
| HEPES | 6.6 |
| Phenol Red•Na | 0.001242 |
| Putrescine•2HCl | 0.000161 |
| Pyruvic acid•Na | 0.055 |
| Thioctic acid | 0.000206 |
| Thymidine | 0.000727 |

It can also be a modified commercially available medium, for example the MCDB153 medium also further including amino acids, for example tyrosine, methionine or a mixture thereof, additional inorganic salts, for example sodium bicarbonate (NaHCO$_3$).

In the presently disclosed subject matter, the medium M3 can also include at least one supplement chosen from bovine pituitary extract (BPE), insulin, penicillin-streptomycin (PS), hydrocortisone, horse serum, calf serum, basic fibroblast growth factor (bFGF), granulocyte macrophage colony stimulating factor (GM-CSF), SCF or any mixture thereof.

In the presently disclosed subject matter, the medium M3 can include from 0.1% to 10% by weight, from 0.5 to 5% by weight, or 1% by weight of penicillin-streptomycin (PS) relative to the total weight of the medium.

In the presently disclosed subject matter, the medium M3 can include a hydrocortisone concentration of from 1.25 to 1.60 μA, from 1.40 to 1.55 μA, or 1.45 μM.

In the presently disclosed subject matter, the medium M3 can include a bovine pituitary extract (BPE) concentration of from 100 to 160 μg·mL$^{-1}$, from 110 to 150 μg·mL$^{-1}$, or equal to 140 μg·mL$^{-1}$.

In the presently disclosed subject matter, the medium M3 can include an insulin concentration of from 15 to 25 μg·mL$^{-1}$, or equal to 20 μg·mL$^{-1}$.

In the presently disclosed subject matter, the medium M3 can include a GM-CSF concentration of from 0.01 to 0.2 μg·mL$^{-1}$, from 0.01 to 0.1 μg·mL$^{-1}$, or equal to 0.01 μg·mL$^{-1}$.

In the presently disclosed subject matter, the medium M3 can include an SCF concentration of from 0.004 to 0.2 μg·mL$^{-1}$, from 0.01 to 0.15 μg·mL$^{-1}$, or equal to 0.05 μg·mL$^{-1}$.

In the presently disclosed subject matter, the medium M3 can include a bFGF concentration of from 0.1 to 10 ng·mL$^{-1}$, from 0.5 to 5 ng·mL$^{-1}$, from 0.8 to 2 ng·mL$^{-1}$, or equal to 1 ng·mL$^{-1}$.

In the presently disclosed subject matter, the medium M3 can include from 1% to 5% by weight, from 2% to 4% by weight, or 3% by weight of horse or calf serum relative to the total weight of the medium.

In the presently disclosed subject matter, the medium M3 and/or all or most of the constituents thereof can be of clinical grade.

In the presently disclosed subject matter, the melanocyte culture step d. can be carried out at an ambient temperature, for example at a temperature of 30 to 40° C., for example equal to 37° C.

In the presently disclosed subject matter, the culture time of step d. can be between 15 and 28 days.

In the presently disclosed subject matter, the melanocyte culture of step d. can be carried out under a controlled atmosphere including at least 5% of CO$_2$.

According to some embodiments, the melanocytes obtained by culture according to step d. can form a cell layer at confluence in the culture container. For example, the melanocytes can form a cell layer of 50% to 100% confluence.

According to some embodiments, when the culture according to step d. corresponds to a cell layer optionally at confluence, the method can also include:
- a step d' of removal of the culture medium, rinsing of the cells with a solution, and removal of the rinsing solution,
- a step d" of detachment of the cells by trypsinization, and
- a pelleting step d"'.

In the presently disclosed subject matter, in step d', the removal of the culture medium can be carried out by any suitable method known to those with ordinary skill in the art. It can for example be suctioning of the medium, or turning the container upside-down in order to remove the culture medium.

In the presently disclosed subject matter, in step d', the rinsing of the cells can be carried out by any method known to those with ordinary skill in the art, for example by sprinkling, or dipping the cells in a rinsing solution.

In the presently disclosed subject matter, the term "melanocyte rinsing solution" is intended to mean any melanocyte rinsing solution known to those with ordinary skill in the art. It can for example be an HBSS buffer solution, for example the solution described in table 2 above, or phosphate buffered saline (PBS) at a pH included from 7.2 to 7.4. It can also be a commercially available buffer solution, for example a phosphate buffered saline (PBS), or a Hank's balanced solution sold respectively by the company Gibco, Sigma Aldrich or Lonza.

In the presently disclosed subject matter, in step d', the removal of the rinsing solution can be carried out by any suitable method known to those with ordinary skill in the art. It can for example be suctioning of the rinsing solution, or turning the container upside-down in order to remove the rinsing solution.

According to some embodiments, the trypsinization step d" can be carried out by immersion of the cells in a buffer solution (BS) including trypsin, followed by the addition of fetal calf serum (FCS) in order to stop the enzymatic reaction.

According to some embodiments, the buffer solution (BS) can be a buffer solution as defined above.

According to some embodiments, the amount of trypsin added to the buffer solution (BS) can be from 0.01% to 0.05% by weight relative to the total weight.

According to some embodiments, the trypsin incubation time before addition of the FCS to the buffer solution can be from 2 to 5 min.

In the presently disclosed subject matter, the amount of FCS added to the solution (BS) can include from 5% to 20% by volume relative to the total volume.

According to some embodiments, the pelleting step d"' can be carried out by sedimentation, by centrifugation by any method known to those with ordinary skill in the art. It can for example be centrifugation at a speed of from 800 to 1200 revolutions per minute.

According to some embodiments, the centrifugation step d"' can be carried out for a period of from 5 to 10 min.

In the presently disclosed subject matter, the centrifugation step d"' can be carried out by any device known to those with ordinary skill in the art. It can for example be a rotary centrifuge sold by the company Eppendorf or Jouan.

In the presently disclosed subject matter, the centrifugation step d"' makes it possible to sediment the cells in order to separate them from the medium. Those with ordinary skill in the art, by virtue of the general knowledge, will know how to adapt/modify the centrifugation step d" using any known technique which makes it possible to sediment cells in a medium.

According to some embodiments, the keratinocyte culture step e. can be carried out in any suitable culture container known to those with ordinary skill in the art. It can be a petri dish, or a culture flask with a capacity of from 25 to 75 cm$^2$, of 25, 75 or 125 cm$^2$.

In the presently disclosed subject matter, the keratinocyte culture medium M4 can be any medium known to those with ordinary skill in the art that is suitable for the culture of keratinocytes. It can for example be a commercially available medium, for example a KSFM medium sold by the company Life-Technology, KGM sold by the company Lonza, or Provitro in an MCDB 153 medium sold by the company Sigma-Aldrich including in particular a mixture of amino acids, of vitamins, of inorganic salts of sugars, for example glucose. It can also be a modified commercially available medium, for example the MCDB153 medium including a sodium chloride concentration of 0.100 to 0.110 M/l, for example of 0.104 M/l, a Hepes concentration of 2 to $3\times10^{-2}$ M/l, for example of $2.29\times10^{-2}$ M/l, a sodium bicarbonate concentration of $1.10\times10^{-2}$ M/l to $1.25\times10^{-2}$ M/l, for example of $1.19\times10^{-2}$ M/l, and including a concentration of arginine, histidine, isoleucine, leucine, methionine, phenylalanine, threonine, tryptophan, tyrosine, valine and choline which is double that of the concentrations of the unmodified MCDB153 medium.

In the presently disclosed subject matter, the medium M4 can also include supplements chosen from growth factors, for example epithelial growth factor (EGF), bovine pituitary extract (BPE), insulin, penicillin-streptomycin (PS), hydrocortisone or any mixture thereof. Advantageously, the medium M4 can include supplements of clinical grade. They can for example be supplements chosen from growth factors, for example epithelial growth factor (EGF), insulin, penicillin-streptomycin (PS), hydrocortisone or any mixture thereof.

In the presently disclosed subject matter, the medium M4 can include for example from 0.5% to 5% by weight, from 0.75% to 3% by weight, or 1% by weight of penicillin-streptomycin (PS) relative to the total weight of the medium.

In the presently disclosed subject matter, the medium M4 can include a hydrocortisone concentration of from 1.25 to 1.60 µM, from 1.40 to 1.55 µM, or of 1.45 µM.

In the presently disclosed subject matter, the medium M4 can include a bovine pituitary extract (BPE) concentration of from 50 to 90 µg·mL$^{-1}$, from 60 to 80 µg·mL$^{-1}$, or of 70 µg·mL$^{-1}$.

In the presently disclosed subject matter, the medium M4 can include an insulin concentration of from 3 to 8 µg·mL$^{-1}$, for example equal to 5 µg·mL$^{-1}$.

In the presently disclosed subject matter, the medium M4 can include an epithelial growth factor (EGF) concentration of from 5 to 15 ng·mL$^{-1}$, from 6.5 to 13 ng·mL$^{-1}$, or equal to 10 ng·mL$^{-1}$.

In the presently disclosed subject matter, the medium M4 and/or all or most of the constituents thereof can be of clinical grade.

In the presently disclosed subject matter, the keratinocyte culture step e. can be carried out at a temperature of 25 to 39° C., for example equal to 37° C.

In the presently disclosed subject matter, the culture time of step e. can be included from 15 to 28 days.

In the presently disclosed subject matter, the keratinocyte culture of step e. can be carried out under a controlled atmosphere including at least 5% of $CO_2$.

According to some embodiments, the keratinocytes obtained by a culture according to step e. can form a monolayer of cells in the culture container. It can for example be a monolayer of cells that is close to confluence, for example from 50% to 80% confluence in the culture container.

According to some embodiments, when the culture according to step e. corresponds to a monolayer of cells that is close to confluence, preferably from 50% to 80% confluence, the method can also include:

a step e' of removal of the culture medium, rinsing of the cells with a solution, and removal of the rinsing solution, a step e" of detachment of the cells by trypsinization, and a centrifugation step e"'.

In the presently disclosed subject matter, in step e', the removal of the culture medium can be carried out by any suitable method known to those with ordinary skill in the art. It can for example be suctioning of the medium, or turning the container upside-down in order to remove the culture medium.

In the presently disclosed subject matter, in step e', the rinsing of the cells can be carried out by any method known to those with ordinary skill in the art, for example by dipping, sprinkling, or incubation of the cells in a keratinocyte rinsing solution.

In the presently disclosed subject matter, the term "keratinocyte rinsing solution" is intended to mean any keratinocyte rinsing solution known to those with ordinary skill in the art. It can for example be a PBS buffer solution or HBSS buffer solution, for example as described in table 2 above, at a pH included from 7.2 to 7.4. It can also be a commercially available buffer solution, for example a phosphate buffered saline (PBS), or a Hank's balanced solution sold respectively by the company Gibco, Sigma Aldrich or Lonza.

In the presently disclosed subject matter, in step e', the removal of the keratinocyte rinsing solution can be carried out by any suitable method known to those with ordinary skill in the art. It can for example be suctioning of the keratinocyte rinsing solution, or turning the container upside-down in order to remove the keratinocyte rinsing solution.

According to some embodiments, the trypsinization step e" can be carried out by immersion of the cells in a solution (S) including trypsin, followed by the addition of fetal calf serum (FCS) in order to stop the enzymatic reaction.

According to some embodiments, the amount of trypsin added to the solution (S) can be included from 0.01% to 0.05% by weight relative to the total weight of the solution.

According to some embodiments, the trypsin incubation time before addition of the FCS to the medium can be included from 5 to 10 min.

In the presently disclosed subject matter, the amount of FCS added to the solution (S) can be included from 5% to 20% by weight relative to the total weight of the solution.

According to some embodiments, the centrifugation step e" can be carried out by any method known to those with ordinary skill in the art. It can for example be centrifugation at a speed of 800 to 1200 revolutions per minute.

According to some embodiments, the centrifugation step e" can be carried out for a period of 5 to 10 min.

In the presently disclosed subject matter, the centrifugation step e" can be carried out by using any device known to those with ordinary skill in the art. It can for example be a rotary centrifuge sold by the company Eppendorf or Jouan.

In the presently disclosed subject matter, step f. of mixing melanocytes obtained in step d. with keratinocytes obtained in step e. can be carried out by any suitable method known to those with ordinary skill in the art. It can for example be mixing of cells with stirring in a culture medium.

In the presently disclosed subject matter, the mixing of melanocytes and keratinocytes of step f. can be carried out with a melanocytes/keratinocytes ratio by number of 1/20 to 1/15, or equal to 1/19.

Advantageously, the present disclosure demonstrates, surprisingly, that when the mixing of melanocytes and keratinocytes is carried out with a melanocytes/keratinocytes ratio of 1/20 to 1/15, preferably equal to 1/19, the skin substitute obtained has structural/biological characteristics identical to those of a skin in vivo.

In one embodiment, the mixing of melanocytes and keratinocytes of step f. is carried out with a melanocytes/keratinocytes ratio by number of 1/20 to 1/15, or equal to 1/19, and the matrix including collagen is a dermal regeneration matrix as defined above.

In the presently disclosed subject matter, the seeding of the dermal substitute of step g. can be carried out by any method known to those with ordinary skill in the art. It can for example be an application, for example by sprinkling of the culture medium including a mixture of melanocytes and keratinocytes obtained in step f., by deposition by subculturing the cells on the dermal substitute, by pouring out dropwise the culture medium including a mixture of melanocytes and keratinocytes obtained in step f., or by 3D printing for example as described in Wonhye Lee et al. "Multi-layered culture of human skin fibroblasts and keratinocytes through three-dimensional freeform fabrication." Biomaterials, 2009, March; 30(8):1587-95 [9].

In the presently disclosed subject matter, the seeding of the dermal substitute of step g. can be advantageously carried out with a (keratinocytes+melanocytes)/fibroblasts ratio of 9 to 19. The present disclosure, in fact, demonstrates, surprisingly, that when the seeding of step g. is carried out with a (keratinocytes+melanocytes)/fibroblasts ratio of 9 to 19, the skin substitute obtained has structural/biological characteristics identical to those of normal skin.

In one embodiment, the seeding of the dermal substitute of step g. is carried out with a (keratinocytes+melanocytes)/fibroblasts ratio of 9 to 19 and the matrix including collagen is a dermal regeneration matrix as defined above.

In the presently disclosed subject matter, the term "skin culture medium M5" is intended to mean any medium known to those with ordinary skill in the art that is suitable for the culture of skin. It can for example be a commercially available medium, for example a modified Green medium, namely including 2/3 of Dulbecco/Vogt modified Eagle's minimal essential medium (DMEM); 1/3 of Ham's F12 medium and including 10% of fetal calf serum (FCS), which is a custom-made mixture sold by the company Gibco including in particular a mixture of amino acids, of vitamins, of inorganic salts and of sugars, for example glucose. It can also be a modified Green medium, that is to say a Green medium free of cholera toxin and of triodothyronine, or a mixture of Iscove's Modified Dulbecco's Medium (IMDM) and MCDB153 medium including 10% of FCS; or an IMDM/dermalife keratinocyte medium including 10% of FCS, sold respectively by the companies Gibco, Lifescience, Promocell and Sigma Aldrich.

In the presently disclosed subject matter, the medium M5 can likewise also include supplements chosen from hyaluronic acid or a hyaluronate or a derivative thereof, ascorbic acid or an ascorbate or a derivative thereof, or a mixture thereof.

In the presently disclosed subject matter, the medium M5 can include for example from 40 to 60 mg·L$^{-1}$, from 45 to 55 mg·L$^{-1}$, or 50 mg·L$^{-1}$ of hyaluronate or hyaluronic acid.

Advantageously, when the medium M5 includes hyaluronic acid or a hyaluronate and/or a derivative thereof, it does not include bovine pituitary extract.

In the presently disclosed subject matter, the medium M5 can include for example from 40 to 60 mg·L$^{-1}$, from 45 to 55 mg·L$^{-1}$, or 50 mg·L$^{-1}$ of ascorbic acid or ascorbate.

In the presently disclosed subject matter, the skin culture step h. can be carried out at a temperature included from 25 to 40° C., for example equal to 37° C.

In the presently disclosed subject matter, the skin culture time of step h. can be between 6 and 21 days, for example from 8 to 15 days.

In the presently disclosed subject matter, the skin culture of step h. can be carried out under a controlled atmosphere including at least 5% of $CO_2$.

According to some embodiments, the skin culture of step h. can be carried out at a temperature included from 25 to 40° C., for example equal to 37° C. and under a controlled atmosphere including at least 5% of $CO_2$ In the presently disclosed subject matter, the medium M5 and/or each of the components thereof can be of clinical grade.

In the presently disclosed subject matter step h. can include:
- a first culture step h.' of at least 6 hours, preferably from 6 to 24 hours, in the presence of a culture medium $M5^1$ including neither hyaluronic acid, nor hyaluronate, nor ascorbic acid nor ascorbate,
- a second culture step h." of 0 to 7 days, preferably of at least 2 days, in the presence of a culture medium $M5^2$ including hyaluronic acid or a hyaluronate or a derivative thereof, and
- a third culture step h.''' of at least two days in a medium $M5^3$ including hyaluronic acid or a hyaluronate or a derivative thereof, and ascorbic acid or an ascorbate or a derivative thereof.

The skin substitute culture medium $M5^1$ corresponds to the medium M5 as defined above including neither ascorbic acid nor ascorbate nor derivatives thereof.

In the presently disclosed subject matter, the medium $M5^1$ and/or each of the components thereof can be of clinical grade.

The skin substitute culture medium $M5^2$ corresponds to the medium M5 as defined above including hyaluronic acid or a hyaluronate or a derivative thereof, while at the same time being free of ascorbic acid, of ascorbate and of a derivative thereof.

In the presently disclosed subject matter, the medium $M5^2$ and/or each of the components thereof can be of clinical grade.

The skin substitute culture medium $M5^3$ corresponds to the medium M5 as defined above including hyaluronic acid or a hyaluronate or a derivative thereof and ascorbic acid or ascorbate or a derivative thereof.

In the presently disclosed subject matter, the medium $M5^3$ can be a medium of clinical grade.

In the presently disclosed subject matter, the culture step h' can be carried out by deposition in a culture medium $M5^1$ of the seeded dermal substitute obtained in step g.

In the presently disclosed subject matter, the culture step h'. can be carried out at a temperature included from 25 to 40° C., for example equal to 37° C.

In the presently disclosed subject matter, the duration of the culture step h'. can be from 6 to 24 hours, for example from 8 to 24 hours, or from 12 to 18 hours.

In the presently disclosed subject matter, the skin culture step h'. can be carried out under a controlled atmosphere including at least 5% of $CO_2$.

Advantageously, the present disclosure demonstrates that step h' makes it possible to promote the adhesion of the melanocytes and keratinocytes on the dermal substitute.

In the presently disclosed subject matter, the culture step h". can be carried out by deposition in a culture medium $M5^2$ of the seeded dermal substitute obtained in step h'. or immersion or submersion of the seeded dermal substitute obtained in step h' in a culture medium $M5^2$.

In the presently disclosed subject matter, the culture step h". can be carried out at a temperature included from 25 to 40° C., for example equal to 37° C.

In the presently disclosed subject matter, the duration of the culture step h". can be included from 0 to 7 days, preferably from 2 to 7 days.

In the presently disclosed subject matter, the skin culture step h". can be carried out under controlled atmosphere including at least 5% of $CO_2$.

In the presently disclosed subject matter, the culture step h'''. can be carried out by a deposition in a culture medium $M5^2$ of the seeded dermal substitute obtained in step h"., immersion of the seeded dermal substitute obtained in step h" in a culture medium $M5^2$, or immersion of the seeded dermal substitute obtained in step h"., said substitute being immersed in said medium up to the air-liquid interface, or so as to just break the surface of said medium.

In the presently disclosed subject matter, the term "breaking the surface of said medium" is intended to mean the immersion of the substitute in the medium in such a way as to cover the substitute over the entirety of its height without immersion of its upper part.

In the presently disclosed subject matter, the culture step h'''. can be carried out at a temperature included from 25 to 40° C., for example equal to 37° C.

In the presently disclosed subject matter, the duration of the culture step h". can include from 2 to 7 days, preferably 7 days.

In the presently disclosed subject matter, the skin culture step h". can be carried out under a controlled atmosphere including at least 5% of $CO_2$.

Advantageously, the present disclosure demonstrates that the immersion of the seeded dermal substitute obtained in step h". in a culture medium $M5^3$ including hyaluronic acid or a hyaluronate or a derivative thereof and ascorbic acid or an ascorbate or a derivative thereof makes it possible to promote the formation of the dermal-epidermal junction and thus provides better polarization of the cells of the seeded dermal substitute.

Advantageously, the present disclosure also demonstrates that the immersion up to the air-liquid interface or just breaking the surface of the medium of the seeded dermal substitute obtained in step h". in a culture medium $M5^3$ including hyaluronic acid or a hyaluronate or a derivative thereof and ascorbic acid or an ascorbate or a derivative thereof enables the epidermis to be differentiated, thus promoting the formation of a horny layer on the skin substitute or equivalent.

Advantageously, the present disclosure also demonstrates that the immersion up to the air-liquid interface or just breaking the surface of the medium of the seeded dermal substitute obtained in step h" in a culture medium $M5^3$ including hyaluronic acid or a hyaluronate or a derivative thereof and ascorbic acid or an ascorbate or a derivative thereof makes it possible to maintain the high proliferative capacity of the cells of the basal layer and a decreasing gradient of proliferative capacity concomitant with the increase in differentiation of the epidermis similar to the gradients observed in the skin in vivo.

Advantageously, the present disclosure also demonstrates that, when the medium M5 includes hyaluronic acid or a hyaluronate or a derivative thereof, this makes it possible, surprisingly, to improve the quality of the skin substitute or equivalent.

Advantageously, the present disclosure also demonstrates that the method advantageously makes it possible to obtain a skin substitute or equivalent including all or most of the constituent layers thereof. Thus, the skin substitute obtained according to the method of some embodiments has characteristics similar to those of native skin, contrary to the skin substitutes known in the related art.

Advantageously, the present disclosure also demonstrates that the method makes it possible to obtain a dermal substitute and/or a skin substitute that is much larger in size than those known in the related art. In particular, the method advantageously makes it possible to obtain a dermal substitute and/or a skin substitute with a surface area of 1 to 25 $cm^2$, for example of 5 to 25 $cm^2$.

The present disclosure also demonstrates that the method makes it possible to obtain a dermal substitute or equivalent and/or a skin equivalent or substitute with a minimum amplification capacity of 6.

In addition, the present disclosure also advantageously demonstrates that the method according to some embodiments makes it possible to obtain a dermal and/or skin substitute that can be handled with viscoelastic properties that advantageously make it possible to avoid any tearing/physical alteration of said substitute during handling thereof.

In addition, the dermal and/or skin substitute preparation time according to the method of some embodiments is typically less than 30 days, and is therefore compatible with the requirements for the care of burns in particular.

A subject of the presently disclosed subject matter is also a skin substitute that can be obtained by implementing the method as defined above.

Advantageously, the present disclosure demonstrates that the skin substitute includes melanocytes at the level of the basal stratum forming an epidermal melanization unit.

Advantageously, the skin substitute that can be obtained by the method of some embodiments advantageously exhibits constitutive pigmentation by virtue of the presence of melanocytes.

Advantageously, the skin substitute is much larger in size than those known in the related art, allowing, in particular when there are extensive wounds, the application of a single or of a smaller number of skin substitutes compared with those of the related art. The decrease in the number of skin substitutes to be applied also advantageously makes it possible to reduce the treatment costs while at the same time accelerating said treatment.

A subject of the presently disclosed subject matter is also a dermal substitute that can be obtained in step c. of the method.

Advantageously, the dermal substitute can include neoformed type IV collagen.

Advantageously, the dermal substitute includes at least one matrix including type I collagen in which the fibroblasts are distributed. It can also contain other extracellular matrix constituents, for example molecules such as collagens, in particular collagen IV, laminins or glycosaminoglycans.

Advantageously, the dermal substitute is much larger in size than those known in the related art, allowing, in particular, when there are extensive wounds, the application of a single or of a smaller number of substitutes compared with those of the related art. The decrease in the number of substitutes to be applied also advantageously makes it possible to reduce the treatment costs while at the same time accelerating the treatment, by virtue, for example, of the provision of a single device covering the entire surface to be treated.

The present disclosure also demonstrates that the dermal substitute and/or the skin substitute according to some embodiments can be advantageously used for the coverage of losses of substance; the dermal substitute and/or the skin substitute according to some embodiments can thus be advantageously used as a graft.

A subject of the presently disclosed subject matter is thus also a graft constituted of a skin substitute as defined above or a dermal substitute as defined above.

In the presently disclosed subject matter, the graft according to some embodiments can be used for treating a skin disorder and/or a loss of skin substance. In particular, the graft according to some embodiments can be used for treating the skin disorder and/or a loss of skin substance chosen from the group including a burn, a healing defect, associated with a trauma wound or with a chronic wound, a pigmentary disorder, a hemangioma and a skin cancer.

A subject of the presently disclosed subject matter is thus also a method for treating a skin ailment, including the transplantation or the implantation of a skin substitute or of a dermal substitute according to some embodiments.

In the presently disclosed subject matter, the implantation of the skin substitute can be carried out by any method known to those with ordinary skill in the art. It can for example be the direct application of the substitute to the area to be treated, for example according to the method described in Pena, and al. Use of Autologous Skin Equivalents With Artificial Dermal Matrix (Integra) in Donor Site Coverage in Radial Forearm Free Flaps: Preliminary Cases J Oral and Maxillofacial Surgery, 70:10 10, 2012 [10].

In the presently disclosed subject matter, the transplantation of the skin substitute can be carried out by any method known to those with ordinary skill in the art. It can for example be a method including a first step of determination and removal of an area of skin/dermis to be removed, followed by a second step of incorporation of the substitute into the area left free. It can also be the method described in the document E. Dantzer, F. Braye Reconstructive surgery using an artificial dermis (Integra): results with 39 grafts. Br J Plast Surg, 54:8 8, 2001 [11].

In the treatment method, the term "skin ailment" is intended to mean a burn, a healing defect associated with a trauma wound or with a chronic wound, a pigmentary disorder, a hemangioma and a skin cancer.

The treatment method can thus allow the replacement of lesioned and/or damaged and/or pathological skin with a healthy skin substitute.

The treatment method can include the transplantation of the skin substitute after ablation, for example of a melanocytic nevus, of a giant melanocytic nevus, of a melanoma, of a hemangioma, or of an eccrine poroma.

The treatment method can also include the implantation and/or the application of a skin substitute onto a burn and/or a deep injury and/or a chronic wound, for example a diabetic wound.

Advantageously, the present disclosure also demonstrates, surprisingly, when the skin substitute or equivalent has been obtained according to the method of some embodiments in which the medium M5 includes hyaluronic acid or a hyaluronate or a derivative thereof, an acceleration of the tissue repair, in particular during the treatment of a skin disorder.

A subject of the presently disclosed subject matter is also a kit for implementing the method according to some embodiments, including a fibroblast culture medium M1, a matrix including collagen, a medium M2 for culture of the fibroblasts in the matrix including ascorbic acid or ascorbate or a derivative thereof, a melanocyte culture medium M3, a keratinocyte culture medium M4 and a skin culture medium M5.

A subject of the presently disclosed subject matter is also a kit for implementing the method according to some embodiments, including a fibroblast culture medium M1, a matrix including collagen, a medium $M2^1$, a medium $M2^2$ for culture of the fibroblasts in the matrix including collagen, a melanocyte culture medium M3, a keratinocyte culture medium M4, a skin culture medium $M5^1$ and/or a skin culture medium $M5^2$ and/or a skin culture medium $M5^3$.

The media M1, M2, $M2^1$, $M2^2$, M3, M4, M5, $M5^1$, $M5^2$ and $M5^3$ are as defined above.

The subject of the presently disclosed subject matter is also a skin grafting method including the steps of:
  taking a skin sample from an unaffected area in an individual,
  preparing a skin substitute according to some embodiments using the fibroblasts, keratinocytes and fibroblasts from the sample taken, and
  grafting the substitute obtained onto the individual.

Other advantages can further emerge to those with ordinary skill in the art on reading the examples below, illustrated by the appended figures, given by way of illustration.

BRIEF DESCRIPTION OF THE DRAWINGS

FIG. 5A shows the substitute colonized by murine fibroblasts. FIG. 5B shows the substitute colonized with human fibroblasts before grafting.

FIGS. 6E and 6F represent optical microscopy photographs of skin after immunohistochemical labeling of the melanocytes in the basal position (FIG. 6E, light areas), labeling of collagen IV (FIG. 6F (2)) and of the p63 proliferation marker (FIG. 6F (1)).

DETAILED DESCRIPTION OF EXEMPLARY EMBODIMENTS

Figure 1:
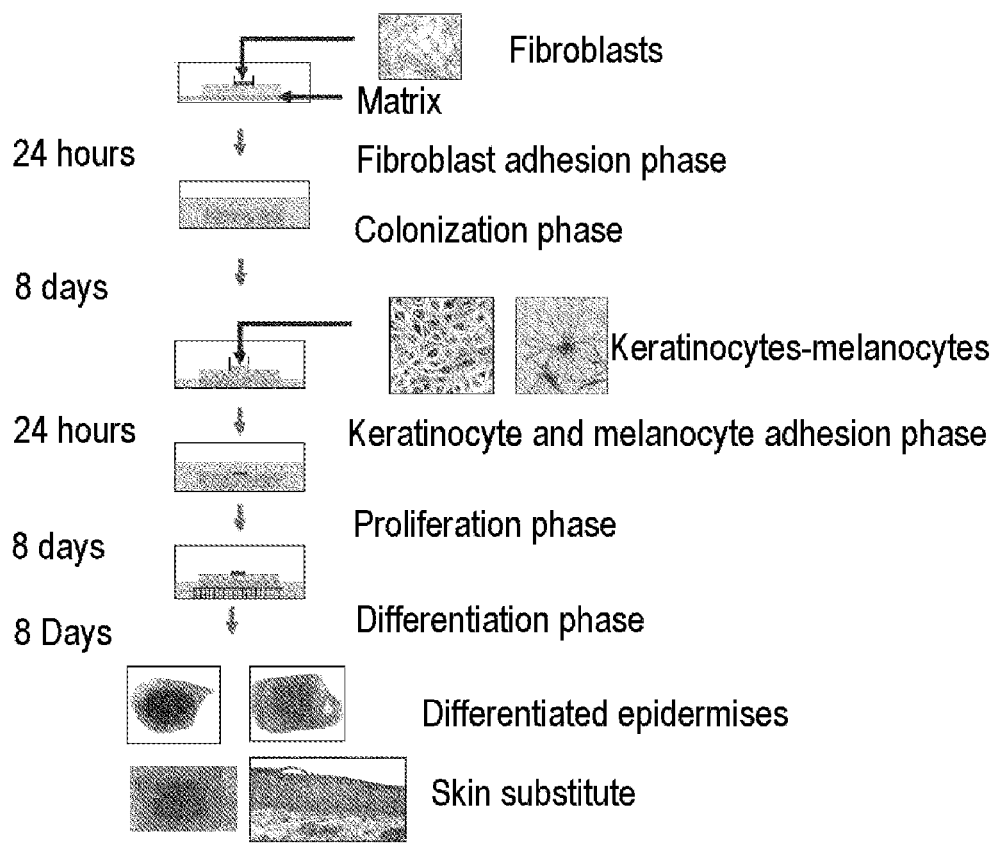
FIG. 1 represents a diagram of the steps for obtaining a skin substitute/equivalent.

A few inventive aspects of the disclosed embodiments are explained in detail below with reference to the various figures. Exemplary embodiments are described to illustrate the disclosed subject matter, not to limit its scope, which is defined by the claims. Those of ordinary skill in the art will recognize a number of equivalent variations of the various features provided in the description that follows.

EXAMPLES

Example 1: Example of Production of a Skin Substitute

In the present example, the cells used came from a skin biopsy taken from mammoplasties previously carried out on a patient.

The biopsy was taken by a plastic surgeon and the biopsy was placed in a sterile tube containing physiological saline.

The cells were isolated from the biopsy as follows:

1. Epithelial Cell Isolation a. Rinsing of the biopsy in sterile HBSS (Hank's Balanced Salt Solution).

b. Removal of the adipose tissue by a biologist-technician using a scalpel.

c. Incubation with trypsin-EDTA preheated to 37° C., for between 3 and 24 h.

d. Neutralization with irradiated FCS (trypsin inhibitor).

e. Removal of the epidermis and scraping, with a scalpel, of the basal stratum where the highly proliferative (p63 positive) cells are found.

f. Filtration, centrifugation at 1200 revolutions per minute and seeding of the pellet at 100 000 cells per cm² in modified* MCDB153 medium including the compounds mentioned in table 4 below in which the concentrations of L-arginine, L-histidine, L-isoleucine, L-leucine, L-methionine, L-phenylalanine, L-threonine, L-tryptophan, L-tyrosine, L-valine and choline chloride have been doubled, the NaCl concentration has been reduced to 0.104 M/l, Hepes has been reduced to $2.29 \times 10^{-2}$ M/l and $NaHCO_3$ has been reduced to $1.19 \times 10^{-2}$ M/l, the pH of the medium being adjusted to 7.4 and antibiotics (penicillin and streptomycin 1%) for the keratinocytes.

For the melanocytes, filtration, centrifugation at 1200 revolutions per minute and seeding of the pellet at 100 000 cells per cm² in modified* MCDB153 medium including the compounds mentioned in table 4 below, also including 5.88 g of sodium bicarbonate/5 l, 0.272 g of tyrosine/5 l and 0.157 g of L-methionine/5 l. the pH of the medium being adjusted to 7.4.

TABLE 4 normal composition of the MCDB 153 medium

| Composition | Concentration in g · l$^{-1}$ |
|---|---|
| Ammonium Metavanadate | 0.000000585 |
| Anhydrous calcium chloride• | 0.00333 |
| Cupric Sulfate•5H$_2$O | 0.00000275 |
| Ferrous sulfate•7H$_2$O | 0.00139 |
| Magnesium chloride | 0.05713 |
| Manganese Sulfate | 0.000000151 |
| Molybdic Acid•4H$_2$O (ammonium) | 0.00000124 |
| Nickel Chloride•6H$_2$O | 0.00000012 |
| Potassium Chloride | 0.11183 |
| Sodium Acetate (anhydrous) | 0.30153 |
| Sodium Chloride | 7.599 |
| Sodium Metasilicate•9H$_2$O | 0.000142 |
| Dibasic Sodium Phosphate (anhydrous) | 0.284088 |
| Sodium Selenite | 0.0000038 |
| Stannous Chloride•2H$_2$O | 0.000000113 |
| Zinc Sulfate•7H$_2$O | 0.000144 |
| L-Alanine | 0.00891 |
| L-Arginine•HCl | 0.2107 |
| L-Asparagine•H$_2$O | 0.015 |
| L-Aspartic Acid | 0.00399 |
| L-Cysteine•HCl•H$_2$O | 0.04204 |
| L-Glutamic Acid | 0.01471 |
| L-Glutamine | 0.8772 |
| Glycine | 0.00751 |
| L-Histidine•HCl•H$_2$O | 0.01677 |
| L-Isoleucine | 0.001968 |
| L-Leucine | 0.0656 |
| L-Lysine•HCl | 0.01827 |
| L-Methionine | 0.00448 |
| L-Phenylalanine | 0.00496 |
| L-Proline | 0.03453 |
| L-Serine | 0.06306 |
| L-Threonine | 0.01191 |
| L-Tryptophan | 0.00306 |
| L-Tyrosine•2Na | 0.00341 |
| L-Valine | 0.03513 |
| D-Biotin | 0.0000146 |
| Choline Chloride | 0.01396 |
| Folic acid | 0.00079 |
| myo-Inositol | 0.01802 |
| Niacinamide | 0.00003663 |
| D-Pantothenic Acid (hemicalcium) | 0.000238 |
| Pyridoxine•HCl | 0.00006171 |
| Riboflavin | 0.0000376 |
| Thiamine•HCl | 0.000337 |
| Vitamin B-12 | 0.000407 |
| Adenine•HCl | 0.03088 |
| D-Glucose | 1.081 |
| HEPES | 6.6 |
| Phenol Red•Na | 0.001242 |
| Putrescine•2HCl | 0.000161 |
| Pyruvic acid•Na | 0.055 |
| Thioctic acid | 0.000206 |
| Thymidine | 0.000727 | g. Incubation at 37° C. at 5% CO$_2$ for one week with medium changed every three days.

h. After approximately one week: differential trypsinization=trypsinization with 0.025% trypsin and 0.0.1 M EDTA (1-2 minutes in order to detach the melanocytes, 10 minutes in order to detach the keratinocytes). The melanocytes detach first, thereby making it possible to purify the cultures.

Neutralization with irradiated FCS, centrifugation at 1200 revolutions per minute and seeding of the pellet for amplification in the same medium.

i. Incubation at 37° C. at 5% CO$_2$ for one week with medium changed every three days.

2. Fibroblast Isolation a. Rinsing of the dermal part with HBSS.

b. Incubation of the dermis with collagenase at 1% at 37° C. for a maximum of three hours depending on the type of dermis.

c. Neutralization with irradiated FCS.

d. Filtration via a 40 µm cell sieve, centrifugation at 1200 revolutions per minute with a GR 2022 centrifuge for 5 minutes and seeding of the pellet at 100 000 cells per cm$^2$ in DMEM including 10% irradiated FCS and penicillin and streptomycin at 1% for 24 hours.

e. Incubation in a Jouan IG 150 incubator at 37° C., 5% CO$_2$, for one week with medium changed every three days.

3. Preparation of a Skin Substitute a. Trypsinization of the fibroblasts with 0.025% trypsin and 0.0.1 M EDTA for 10 minutes, then neutralization with irradiated FCS, centrifugation at 1200 revolutions per minute with a GR 2022 centrifuge for 5 minutes, and seeding in DMEM including 10% FCS on a dermal matrix of sterile collagen origin, namely an Integra matrix (registered trademark) rinsed beforehand with Hank's Balanced Salt Solution (HBSS) three times, in a proportion of 30 000 fibroblasts per cm$^2$ in a made-to-measure stainless steel incubation chamber.

b. After 24 hours of culture at 37° C., 5% CO$_2$, the incubation chamber was removed from the matrix.

C. The seeded matrix was incubated at 37° C., 5% CO$_2$ in DMEM including 10% of irradiated FCS and penicillin and streptomycin at 1% and 50 mg/mL ascorbic acid, for one week with medium changed every three days.

d. Trypsinization of the keratinocytes and of the melanocytes with 0.025% trypsin and 0.0.1 M EDTA for 1 to 2 minutes in order to detach the melanocytes from the melanocyte culture dishes, for 10 minutes in order to detach the keratinocytes from the keratinocyte culture dishes. Neutralization with irradiated FCS and centrifugation and seeding at 400 000 cells per cm$^2$ in an incubation chamber of a mixture containing 1 melanocyte per 19 keratinocytes.

e. Adhesion for 24 hours.

f. Submersion for seven days in modified green medium: DMEM/Ham's F12/10% FCS including hyaluronic acid at 50 mg/ml.

g. Interface for 7 days in modified Green medium: DMEM/Ham's F12 including 10% FCS, hyaluronic acid at 50 mg/ml and 50 mg/ml ascorbic acid and antibiotics, namely 1% penicillin-streptomycin.

FIG. 1 represents a diagram of the steps for obtaining a skin substitute.

In the present example, two skin substitutes obtained had (keratinocytes+melanocytes)/fibroblasts ratios of 13.3. For the ratio of 13.3, during the steps of depositing the fibroblasts and the keratinocytes/melanocytes mixture, the amounts of cells seeded were respectively 15 000 for the fibroblasts, 10 000 for the melanocytes and 190 000 for the keratinocytes.

Figure 2:
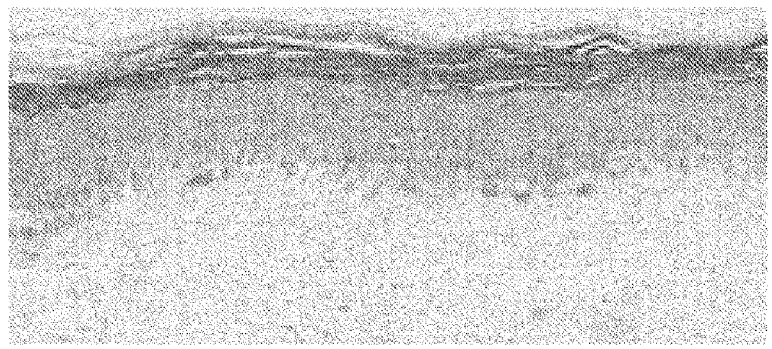
FIG. 2 represents optical microscopy photographs of skin (FIG. 2A), and of skin substitutes obtained according to the method of some embodiments with variations in the ratio of cells seeded (FIGS. 2B and 2C).
Figure 2:
Figure 2:
Figure 3:
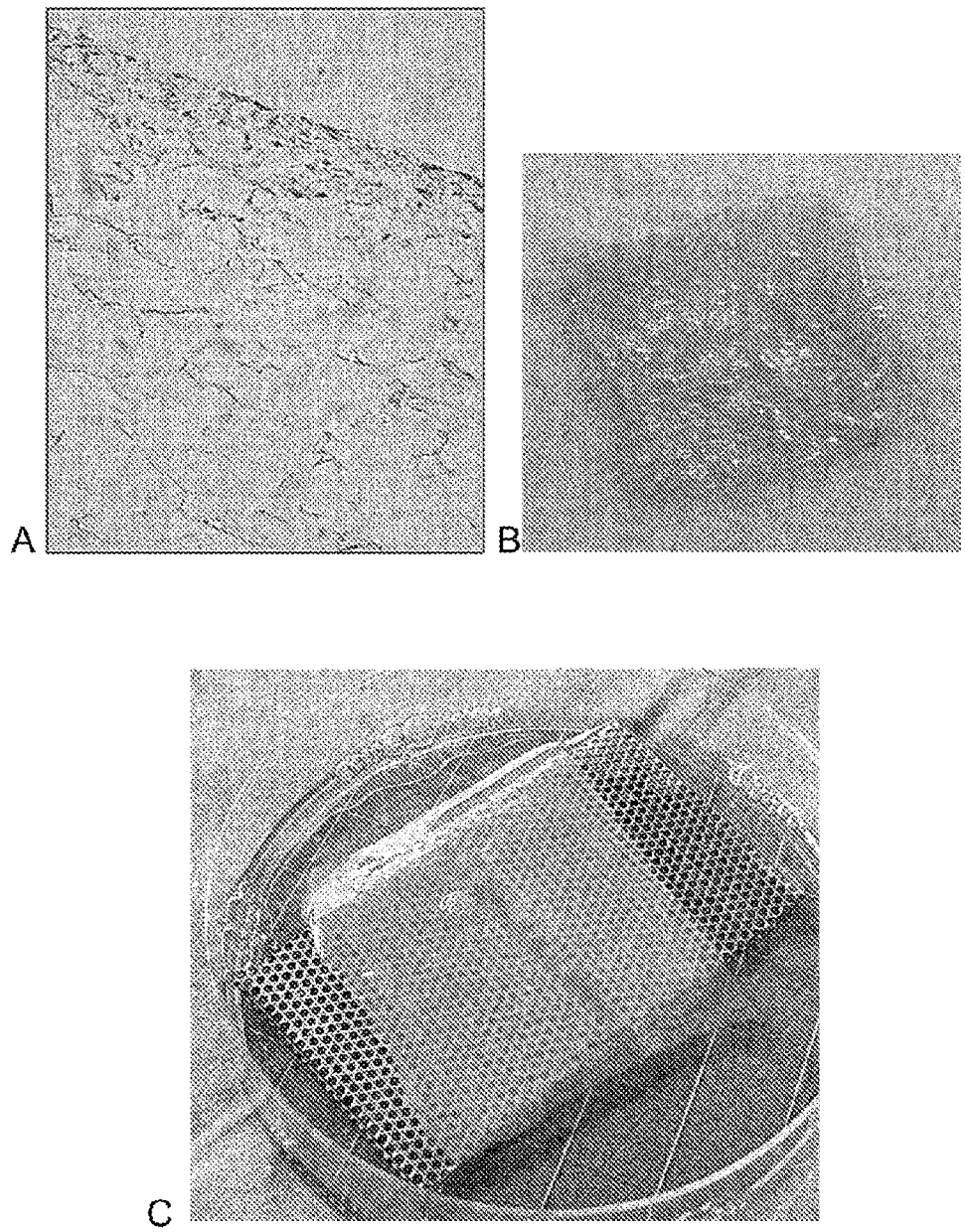
FIG. 3A is a photograph of a dermal substitute obtained in step c, by optical microscopy after staining of the fibroblasts.
FIG. 3B is a photograph of a skin substitute obtained, of small size, namely 0.5 cm².
FIG. 3C is a photograph of a skin substitute obtained, of medium size, namely 25 cm².
Figure 6:
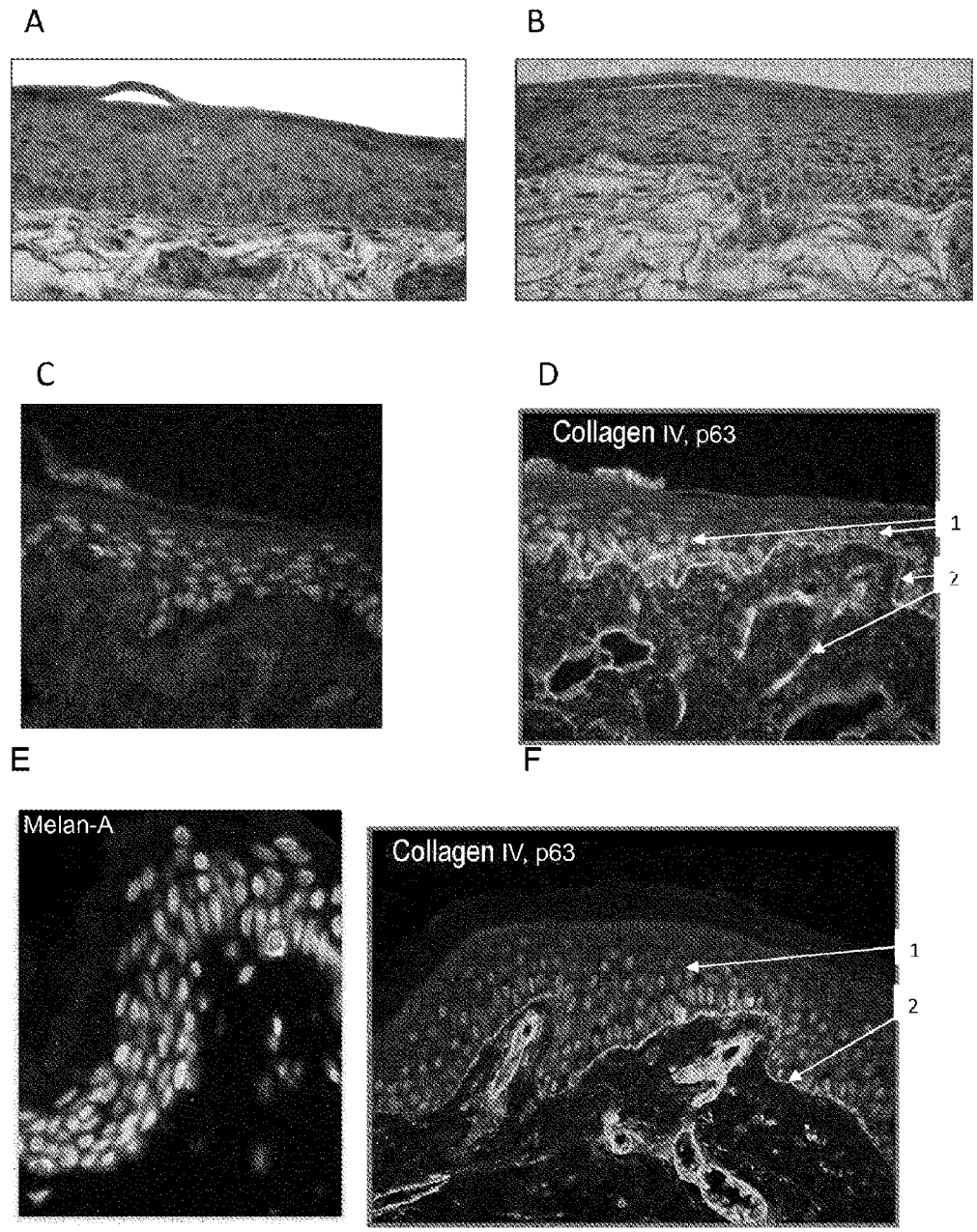
FIG. 6 represents optical microscopy photographs of skin equivalent (FIGS. 6A to D) obtained according to the method with a (keratinocytes+melanocytes)/fibroblasts seeded cell ratio of 13.3 (FIGS. 6A and B); the immunohistochemical labeling of the melanocytes in the basal position (FIG. 6C, light areas) and the production of the basal lamina, labeling of collagen IV (FIG. 6D (2)) and the p63 proliferation marker (FIG. 6 D (1)).

Once the substitute had been obtained, it was fixed in 4% formol, embedded in paraffin, then a 4 µm section was cut, and then hematoxylin-eosin staining was performed in order to label the various layers of the skin. Observation under an optical microscope and at a magnification of ×40 was carried out. Since the microscope was coupled to a CCD camera (Nikon, software NIS element Br), photographs of the observations were taken. FIG. 2B represents an optical microscopy photograph of a skin substitute obtained according to the method in which the (keratinocytes+melanocytes)/fibroblasts ratio was 13.3. FIG. 2C represents an optical microscopy photograph of a skin substitute obtained according to the method in which the (keratinocytes+melanocytes)/ fibroblasts ratio was 6.7 and FIG. 2A represents an optical microscopy photograph of a normal skin biopsy. FIGS. 6A and 6B also represent optical microscopy photographs of a skin equivalent obtained according to the method in which the (keratinocytes+melanocytes)/fibroblasts ratio was 13.3.

Moreover, immunohistochemical labeling of the substitute obtained according to the method in which the (keratinocytes+melanocytes)/fibroblasts ratio was 13.3 and of an in vivo skin was carried out according to the method described in Salducci, M., André, N., Guéré, C., Martin, M., Fitoussi, R., Vié, K., and Cario-André, M. (2014). Factors secreted by irradiated aged fibroblasts induce solar lentigo in pigmented reconstructed epidermis. Pigment Cell Melanoma Res. 27, 502-504 [12] or Simon, D., Daubos, A., Pain, C., Fitoussi, R., Vié, K., Taieb, A., de Benetti, L., and Cario-André, M. (2013). Exposure to acute electromagnetic radiation of mobile phone exposure range alters transiently skin homeostasis of a model of pigmented reconstructed epidermis. Int. J. Cosmet. Sci. 35, 27-34 [13] in order to identify in the substitute the presence of melanocytes, the production of the basal lamina including in particular collagen IV (FIG. 6D (2)), the proliferative capacity of the cells in the basal lamina (FIG. 6D (1)) and the presence of melanocytes (FIG. 6C). FIGS. 6E and 6F represent optical microscopy photographs of skin in vivo after immunohistochemical labeling of the melanocytes in the basal position (FIG. 6E, light areas), labeling of collagen IV (FIG. 6F (2)) and labeling of the p63 proliferation marker (FIG. 6F (1)). It is clearly apparent on FIGS. 6C and 6D that the skin substitute according to some embodiments includes melanocytes, and a basal lamina as demonstrated by the presence of collagen IV at the level of which the cells present are highly proliferative as for the skin in vivo (FIGS. 6E and 6F).

As represented on these photographs, the substitute obtained by the method has a structure identical to that of the skin in vivo.

Example 2: Grafting of a Dermal Substitute According to Some Embodiments onto Mice In this example, the skin substitute used was the substitute obtained as described in example 1 with cells obtained from mammoplasties with the (keratinocytes+melanocytes)/fibroblasts ratio of 13.3. The mice used were swiww nu/nu nude mice from Jackson Lab.

In this example, grafts were performed on ten mice in parallel.

An incision of the mice was made using a scalpel on an area of 5 cm² in order to eliminate the dermis and the epidermis, and the scarified area was cleaned with physiological saline. A skin substitute previously prepared was applied to the scarified area in order to cover it (FIG. 4 A, row 1) and then the grafted area was closed with the skin of the mouse that was sutured (FIG. 4 B, row 1).

The mice were kept in a specialized animal house one per cage for the time required for the graft to take and then five per cage in cages of appropriate size.

Figure 4:
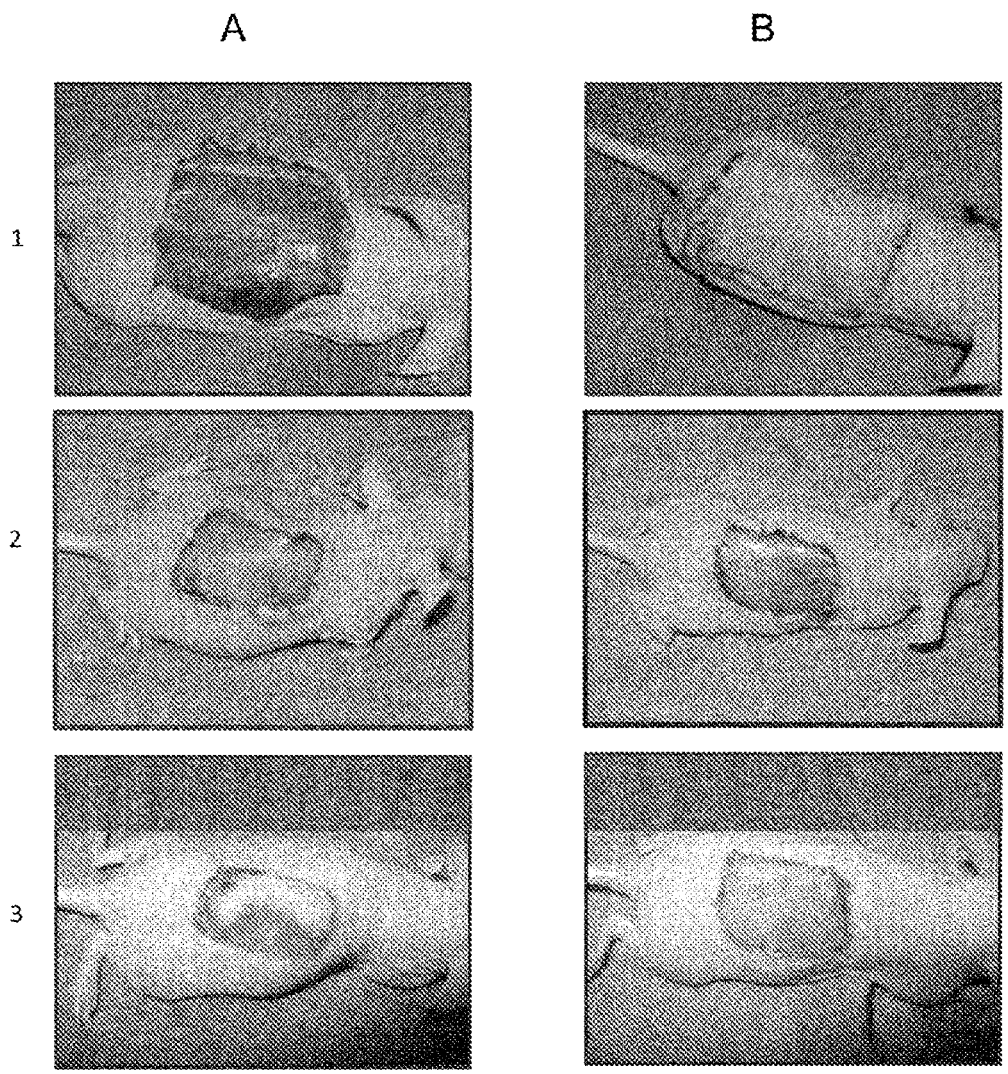
FIG. 4 represents photographs after grafting of a matrix including collagen (column A) or of a dermal substitute obtained in step c (column B) on the day of grafting (row 1), 14 days after grafting (row 2) or 24 days after grafting (row 3).

After two weeks, an observation was made of how the graft had taken by removing the flap of skin from the mouse (FIG. 4 A, row 2). In other words, the sutures were removed from the mouse skin that had been sutured, said skin was removed and the grafted dermal substitute was revealed for visual observation (FIG. 4 B, row 2).

After three weeks, visual observation of how the graft had taken was carried out (FIGS. 4B and B, row 3).

As demonstrated in FIG. 4, it is clearly apparent that the dermal substitute can advantageously be applied, in particular for a graft without induction of side effects.

In addition, in order to study the structural condition of the dermal substitute after three weeks post-application, a sample was taken by cutting the substitute with a scalpel. The substitute was fixed in 4% formol, embedded in paraffin, then a 4 µm section was cut, and then hematoxylin-eosin staining was performed in order to label the various layers of the skin. Observation under an optical microscope at a magnification of ×40 was carried out. Since the microscope was coupled to a CCD camera (Nikon, software NIS element Br), photographs of the observations were taken.

Figure 5:
FIG. 5 represents optical microscopy photographs of a sample taken from the graft 24 hours after grafting, after hematoxylin-eosin staining.
Figure 5:

FIG. 5 represents the optical microscopy photographs of grafted substitutes. In particular, FIG. 5A shows the substitute colonized by the murine fibroblasts of which there are not very many and which have not begun to reorganize the collagen. FIG. 5B shows the substitute colonized with the human fibroblasts before grafting. A large number of fibroblasts and reorganization of the matrix, in particular in the superficial area with thicker bunches of collagen, are observed. The present example thus clearly demonstrates that the presence of all or most of the cells makes it possible to obtain an easily integratable substitute, which does not degrade over time and which exhibits maturation after grafting, which is accelerated in the presence of fibroblasts in the matrix.

LIST OF REFERENCES

1. Pendaries V et al., siRNA-mediated allele-specific inhibition of mutant type VII collagen in dominant dystrophic epidermolysis bullosa.JID 2012, June; 132(6):1741-3.
2. Petek L M et al., "Efficient KRT14 targeting and functional characterization of transplanted human keratinocytes for the treatment of epidermolysis bullosa simplex". Mol ther 2010, September; 18 (9):1624-32.
3. Kogut et al., "Differentiation of human induced pluripotent stem cells into a keratinocyte lineage" Methods Mol Biol 2014, 1195:1-12.
4. Ohta et al., "Generation of human melanocytes from induced pluripotent stem cells" Methods Mol Biol, 2013; 989:193-215.
5. Revilla et al., "Current advances in the generation of human iPS cells: implications in cell-based regenerative medicine." J Tissue Eng Regen Med, 2015, Mar. 11.
6. Bell et al., 1979
7. Boyce S T et al., "Structure of a collagen-GAG dermal skin substitute optimized for cultured human epidermal keratinocytes", 1988 October; 22 (10):939-57.
8. Hafemann et al., "Use of a collagen/elastin-membrane for the tissue engineering of dermis." Burns 1999, August; 25(5):373-84.
9. Wonhye Lee et al., "Multi-layered culture of human skin fibroblasts and keratinocytes through three-dimensional freeform fabrication." Biomaterials, 2009, March; 30(8): 1587-95
10. Pena, and al., J Oral and Maxillofacial Surgery, 70:10 10, 2012
11. E. Dantzer, F. Braye "Reconstructive surgery using an artificial dermis (Integra): results with 39 grafts." Br J Plast Surg, 54:8 8, 2001.
12. Salducci, M., André, N., Guéré, C., Martin, M., Fitoussi, R., Vié, K., and Cario-André, M. (2014). Factors secreted by irradiated aged fibroblasts induce solar lentigo in pigmented reconstructed epidermis. Pigment Cell Melanoma Res. 27, 502-504

13. Simon, D., Daubos, A., Pain, C., Fitoussi, R., Vié, K., Taieb, A., de Benetti, L., and Cario-André, M. (2013). Exposure to acute electromagnetic radiation of mobile phone exposure range alters transiently skin homeostasis of a model of pigmented reconstructed epidermis. Int. J. Cosmet. Sci. 35, 27-34

The invention claimed is:

1. A method for preparing a skin substitute, comprising the steps of:
    a. culturing fibroblasts in a fibroblast culture medium M1;
    b. seeding a matrix including collagen with the fibroblasts obtained in step a;
    c. culturing the fibroblasts seeded in the matrix including collagen obtained in step b in a fibroblast culture medium M2 that includes ascorbic acid, an ascorbate, or a derivative thereof, whereby the matrix and the cultured fibroblasts form a dermal substitute;
    d. culturing melanocytes in a melanocyte culture medium M3;
    e. culturing keratinocytes in a keratinocyte culture medium M4;
    f. mixing the melanocytes obtained in step d with the keratinocytes obtained in step e;
    g. seeding the dermal substitute obtained in step c with the mixture of keratinocytes+melanocytes obtained in step f, wherein the seeding is carried out with a (keratinocytes+melanocytes)/fibroblasts ratio equal to or greater than 9/1 and less than or equal to 19/1; and
    h. culturing the seeded dermal substitute obtained in step g in a skin culture medium M5 thus forming the skin substitute thereof, wherein the medium M5 includes 40 to 60 mg/L of hyaluronic acid, a hyaluronate or a derivative thereof, and 40 to 60 mg/L of ascorbic acid, an ascorbate, a derivative thereof, and the skin substitute provided contains functional basal lamina.

2. The method as claimed in claim 1, wherein the mixing of melanocytes and keratinocytes of step f is carried out with a melanocytes/keratinocytes ratio of 1/20 to 1/15.

3. The method as claimed in claim 1, wherein the seeding in step b is carried out at a density of from 20,000 to 50,000 fibroblasts/cm$^2$ of surface area of the matrix including collagen.

4. The method as claimed in claim 1, wherein step c comprises:
    a first culturing step c' of 18 to 28 hours in the presence of a fibroblast culture medium M21 that includes neither ascorbic acid nor ascorbate, and
    a second culturing step c" of at least two days in the presence of a fibroblast culture medium M2 that includes ascorbic acid, an ascorbate, or a derivative thereof.

5. The method as claimed in claim 1, wherein step h comprises:
    a first culturing step h' of 6 to 24 hours in the presence of a culture medium M51 that includes neither hyaluronic acid, nor hyaluronate, nor ascorbic acid, nor ascorbate, and
    a second culturing step h" of at least 2 days in the presence of a culture medium M52 that includes hyaluronic acid, a hyaluronate, or a derivative thereof, and
    a third culturing step h''' of at least two days in the medium M5 that includes 40 to 60 mg/L hyaluronic acid, hyaluronate, or derivative thereof, and 40 to 60 mg/L ascorbic acid, ascorbate, or derivative thereof.

6. The method as claimed in claim 1, wherein the skin substitute is further provided to contain at least one selected from the group consisting of:
    keratinized pluristratified epithelium with a stratum basal, a stratum spinosum, a stratum granulosum and a stratum corneum.

7. The method as claimed in claim 1, wherein the skin substitute is further provided to contain:
    basal melanocytes in contact with a dermal substitute containing functional fibroblasts.

8. A skin substitute obtained by implementing the method defined in claim 1.

9. The skin substitute as claimed in claim 8, wherein the fibroblasts are autologous to an intended recipient of a graft constituted of said skin substitute.

10. The skin substitute as claimed in claim 9, wherein the fibroblasts, the melanocytes and the keratinocytes are autologous with respect to said intended recipient.

11. A graft constituted of the skin substitute as claimed in claim 9.

12. The graft as claimed in claim 11, wherein said graft is fabricated for use in treating a skin disorder and/or a loss of skin substance.

13. The graft as claimed in claim 12, wherein the skin disorder and/or a loss of skin substance is chosen from the group including a burn, a healing defect, a chronic wound, a pigmentary disorder, a hemangioma and a skin cancer.

* * * * *